(12) United States Patent
Durkin

(10) Patent No.: US 10,821,248 B2
(45) Date of Patent: Nov. 3, 2020

(54) COURIER AIRWAY DEVICE

(71) Applicant: David James Durkin, Boalsburg, PA (US)

(72) Inventor: David James Durkin, Boalsburg, PA (US)

( * ) Notice: Subject to any disclaimer, the term of this patent is extended or adjusted under 35 U.S.C. 154(b) by 249 days.

(21) Appl. No.: 15/425,610

(22) Filed: Feb. 6, 2017

(65) Prior Publication Data

US 2018/0221051 A1 Aug. 9, 2018

(51) Int. Cl.
| | | |
|---|---|---|
| A61M 16/04 | (2006.01) | |
| A61B 5/097 | (2006.01) | |
| A61B 5/08 | (2006.01) | |
| A61B 1/267 | (2006.01) | |
| A61B 8/00 | (2006.01) | |
| A61B 5/083 | (2006.01) | |
| A61M 16/08 | (2006.01) | |

(52) U.S. Cl.
CPC ......... *A61M 16/0409* (2014.02); *A61B 1/267* (2013.01); *A61B 5/082* (2013.01); *A61B 5/097* (2013.01); *A61M 16/0415* (2014.02); *A61M 16/0486* (2014.02); *A61M 16/0493* (2014.02); *A61B 5/0836* (2013.01); *A61B 8/4209* (2013.01); *A61M 16/085* (2014.02); *A61M 2205/05* (2013.01); *A61M 2230/432* (2013.01)

(58) Field of Classification Search
CPC .......... A61M 16/0409; A61M 16/0415; A61M 16/0486; A61M 16/0493; A61B 8/4209
See application file for complete search history.

(56) References Cited

U.S. PATENT DOCUMENTS

| | | | | |
|---|---|---|---|---|
| 3,774,616 A | * | 11/1973 | White | A61M 16/0488 128/200.26 |
| 5,355,879 A | * | 10/1994 | Brain | A61M 16/04 128/207.15 |
| 6,631,720 B1 | | 10/2003 | Brain | |
| 7,004,169 B2 | | 2/2006 | Brain | |
| 7,383,736 B2 | | 6/2008 | Esnouf | |
| 7,762,261 B1 | * | 7/2010 | Fortuna | A61M 16/0409 128/207.14 |
| 8,033,176 B2 | | 10/2011 | Esnouf | |
| 2001/0012923 A1 | * | 8/2001 | Christopher | A61M 16/085 604/48 |

(Continued)

FOREIGN PATENT DOCUMENTS

| | | |
|---|---|---|
| CN | 202961408 U | 6/2013 |
| CN | 204319455 U | 5/2015 |
| WO | 2009/025843 A1 | 2/2009 |

OTHER PUBLICATIONS

International Search Report dated May 8, 2018 for PCT/US2018/016600, filed Feb. 2, 2018, 2 pgs.

(Continued)

*Primary Examiner* — Manuel A Mendez
*Assistant Examiner* — Tasnim Mehjabin Ahmed
(74) *Attorney, Agent, or Firm* — Brooks Kushman P.C.

(57) ABSTRACT

A courier airway device includes a tubular structure that defines a central channel through which a medical diagnostic or therapeutic device can be inserted. The tubular structure also defines a ventilation duct for providing gases from a controlled ventilation machine to a patient. A cuff is attached to the central channel. Characteristically, the cuff is an inflatable balloon-like ring.

25 Claims, 10 Drawing Sheets

(56) References Cited

U.S. PATENT DOCUMENTS

| | | | | |
|---|---|---|---|---|
| 2001/0017135 A1* | 8/2001 | Cook | ............... | A61M 16/0816 |
| | | | | 128/207.15 |
| 2001/0032646 A1* | 10/2001 | Christopher | ...... | A61M 16/0495 |
| | | | | 128/200.26 |
| 2002/0162555 A1* | 11/2002 | West | ................ | A61M 16/0493 |
| | | | | 128/206.29 |
| 2003/0163045 A1* | 8/2003 | Gatzke | ................... | A61B 8/565 |
| | | | | 600/437 |
| 2007/0240722 A1* | 10/2007 | Kessler | ............ | A61M 16/0415 |
| | | | | 128/207.15 |
| 2014/0076309 A1* | 3/2014 | Takeda | .................... | A61F 7/123 |
| | | | | 128/200.26 |
| 2014/0305432 A1 | 10/2014 | Brain | | |
| 2020/0113427 A1* | 4/2020 | Molnar | ............... | A61B 1/0676 |

OTHER PUBLICATIONS https://events.jspargo.com/Anethesiology17/public/eBooth.aspx? BoothID=495542&Task=Products&ProdID=1671&nav=0, Teleflex, Anesthesiology 2017, 3 pgs.

LMA Gastro Cuff Pilot Instructions for Use, 2016, pp. 1-16.

* cited by examiner

COURIER AIRWAY DEVICE

TECHNICAL FIELD

In at least one aspect, the present invention is related to devices to be used to control a patient's ventilation during a medical diagnostic or therapeutic procedure involving the upper gastrointestinal tract.

BACKGROUND

During the last decade, upper gastrointestinal (UGI) endoscopy procedures have shown rapid growth in terms of the numbers performed, as well as the duration and level of complexity of the procedures on an aging population with their associated comorbidities. While UGI endoscopies are essential for the diagnosis, monitoring, and treatment of many conditions, their diagnostic and interventional complications include dental damage, trauma to the tissues of the glottis, laryngospasm and bronchospasm, regurgitation and aspiration, bleeding, infection, and tears of the gastrointestinal wall, stress related cardiovascular events as hypertension, hypotension, tachycardia and other dysthymias, myocardial infarctions and death. Procedural sedation-related complications include drug reactions, hyperventilation, respiratory arrest, loss of protective airway reflexes with resultant aspiration, airway obstruction, hypotension, dysrhythmias, myocardial ischemia and infarction, and death. Comorbidities found in the aging population include: atherosclerosis, heart disease, advanced diabetes, chronic obstructive lung disease, renal impairment and decreased functional reserves, which all contribute to the increased morbidity and mortality of patients undergoing the stresses of upper endoscopy procedures.

Concomitantly as the complexity and duration of UGI procedures is performed on patients with increasing comorbidities, the requirement for anesthesia services, has increased. More and more procedures are being performed, not with moderate sedation, but with deep IV sedation and/or general anesthesia which not only improves patient satisfaction and thus compliance for follow-up procedures, and facilitates optimal conditions for efficiency and better outcomes for the gastroenterologist, but makes available an airway specialist who is dedicated to monitoring and medically treated these patients in response to the rapidly changing conditions during the stresses of the procedure and necessary sedation.

During UGI procedures, the patient is sedated and the gastroenterologist typically advances a ten-millimeter diameter endoscope through the mouth and airway passage, past the glottis, and further down the digestive tract. At times oxygenation and/or ventilation can become suboptimal, and modifications are made, such as increasing oxygen flows, attempted jaw thrust, neck and airway adjustments, insertion of airway devices or nasal trumpets, lessening of sedation, or the removal of the endoscope with laryngoscopy and insertion of an endrotracheal breathing tube into the trachea. But even this can be unsuccessful resulting in a "cannot ventilate, cannot intubate" scenario. Only about 50% of difficult airways are recognized preoperatively even by anesthesiologists, the undisputed airway experts. Airway complications are one of the most common causes of malpractice claims, and many cardiovascular collapses are preceded with a compromised airway. As such, clear communication and cooperation between the anesthesia provider and the gastroenterologist is essential as it can be challenging to perform these airway adjustments while sharing the common limited space between the lips and the glottis with the gastroenterologist.

Accordingly there is an opportunity and a need to design equipment which can improve conditions for upper gastrointestinal procedures, while simultaneously protecting and optimizing the ventilation of the patient, for the ultimate safety and wellbeing of the patient.

SUMMARY

The present invention solves one or more problems of the prior art by providing in at least one embodiment, a courier airway device to protect a patient's airway, and monitor, maintain, optimize, and/or assist or control a patient's ventilation while simultaneously and equally serving as a courier (or guide) for the transport through the oral pharynx of any instrumentation (i.e., medical device), diagnostic, procedural or therapeutic, necessitating access to the UGI tract. The courier airway device includes a tubular structure that defines a central channel through which a medical diagnostic, procedural, or therapeutic device can be inserted. The tubular structure also defines a ventilation duct for providing gases from a controlled ventilation machine to a patient. A cuff is attached to the central channel. Characteristically, the cuff is an inflatable ring. Examples of medical diagnostic devices that can be used with the courier airway device include endoscopes and transesophageal echocardiogram devices.

In another embodiment, a diagnostic and/or therapeutic method using the courier airway device set forth herein is provided. The method includes a step of positioning and securing the courier airway device in the patient such that the cuff is at the level of a patient's glottis, the cuff entering the patient through the patient's oral cavity. After placement, the cuff is inflated. The adjustable bite block and alae are seated in proper position against the patient's teeth and gums, and against the patients mouth and cheeks properly, the head strap placed, and the locking mechanism secured. A portion of the medical device can then be passed through the central channel and into position into the proximal region of a patient's esophagus. The medical procedure can then be performed.

The courier airway device and related methods provide a number of advantages over the prior art. For the gastroenterologist, the courier airway device acts as a courier to assist in the delivery of the endoscopic instruments to the proximal esophagus and more distal structures; diminishes the incidence of soft tissue trauma of the mucous membranes and deeper structures of the oral pharynx, posterior pharynx, and the glottis, especially for procedures requiring multiple insertions or removal of foreign bodies; and diminishes the risk of aspiration by providing a low resistance outlet or channel for gastric fluids and providing an inflatable supraglottis mask over the glottis opening. For the Anesthesiologist, the courier airway device optimizes oxygenation of the spontaneously breathing patient by delivering wall oxygen through a dedicated channel directly to the glottis opening, thus diminishing dead space and rebreathing. Alternatively, the courier airway device can provide for assisted, and/or controlled respirations as needed. If the anesthesiologist desires to assist or control ventilation, an anesthesia circuit is attached to the elbowed standardized connector which is designed to swivel 360 degrees in order to remain out of the operative field of the gastroenterologist.

The patient's respirations are monitored by sampling the end tidal carbon dioxide through a dedicated channel beginning at the level of the glottis.

Oxygen desaturation, retention of $CO_2$, and reduced respiratory drive are major side effects of the deep sedation required for upper endoscopic procedures. The courier airway device can be used in patients that need both optimization of oxygenation and removal of end tidal carbon dioxide for a physiologically stress reduced experience. Advantageously, the courier airway device can be used for patient with comorbidities as: anemia, chronic obstructive pulmonary disease (COPD) and other lung pathology such as restrictive lung disease, obstructive sleep apnea (OSA), morbid obesity, coronary artery disease, congestive heart failure or other cardiac myopathy, pulmonary hypertension, valvular heart disease such as aortic stenosis, and can be used to optimize the patients physiology during complex, prolonged, or painful procedures which often require deep sedation, total intravenous anesthesia (TIVA), or general anesthesia (GA).

In at least one aspect, the present invention is related to devices which serve as a guide to deliver instruments to the upper gastrointestinal tract.

In another aspect, the present invention is related to devices which serve as a channel for an instrument to be inserted into the upper gastrointestinal tract during a medical procedure. In another aspect, the present invention is related to devices to be used to control and/or monitor a patient's ventilation during a medical procedure.

DETAILED DESCRIPTION

Figure 1:
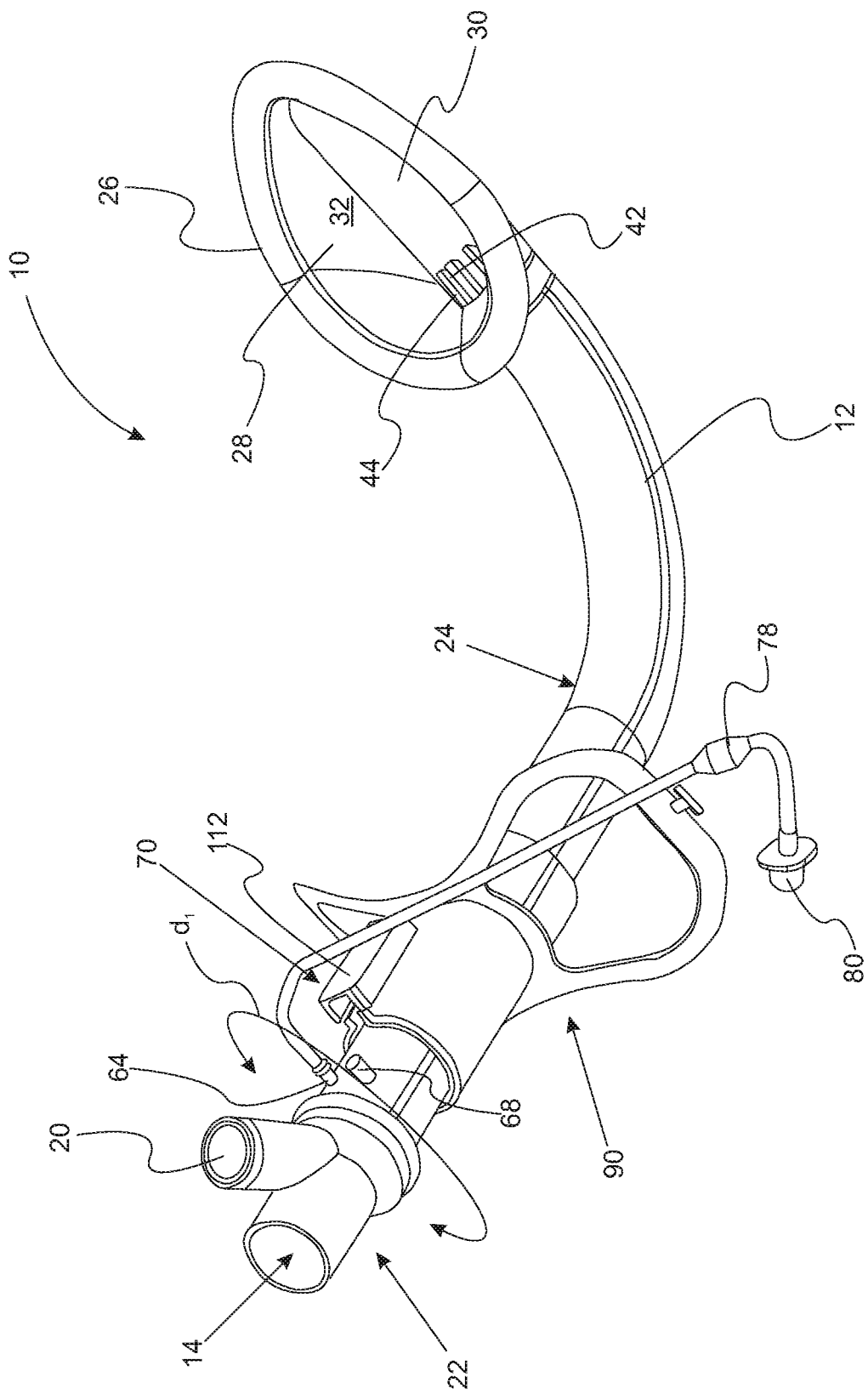
FIG. 1 is a perspective view of a courier airway device.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: the description of a group or class of materials as suitable or preferred for a given purpose in connection with the invention implies that mixtures of any two or more of the members of the group or class are equally suitable or preferred; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

With reference to FIGS. 1, 2A, 2B, and 3, schematic illustrations of the courier airway device with an integrated access tube for passing a medical diagnostic, procedural, or therapeutic device are provided. Courier airway device 10 includes compound tubular structure 12 defining a central channel 14 through which a medical device (i.e., diagnostic, therapeutic, or procedural) can be inserted. Compound tubular structure 12 can be made from any polymeric rubber or plastic, and in particular, a non-allergenic plastic or rubber. Examples of such materials include, but are not limited to, silicone rubber, polyvinyl chloride, polyethylene, polyurethane, and the like. Typically, the material of the inside of central channel 14 has a low coefficient of friction for the medical device (i.e., scope or TEE). Compound tubular structure 12 also defines a ventilation duct (see below) in communication with an angulated ventilation access port 20 for providing gases from a controlled ventilation machine to a patient (e.g., a human or animal patient). In one refinement, ventilation access port 20 of the courier airway device has two distinguishing features which contribute to field avoidance and the optimization of the procedure. First, compound tubular structure 12 is formed from two interlocking components, end component 22 and tubular component 24. Therefore, end component 22 can rotate relative to tubular component 24 along direction $d_1$ thereby allowing ventilation access port 20 to swivel 360 degrees so as to avoid the procedural field of the diagnostician or proceduralist as set forth in more detail below. Second, ventilation access port 20 is angulated away from the center axis of the tube. In another refinement, ventilation access port 20 of courier airway device may not swivel 360 degrees, however remains angulated from the center axis of the tube 14 to enhance field avoidance.

Figure 2:
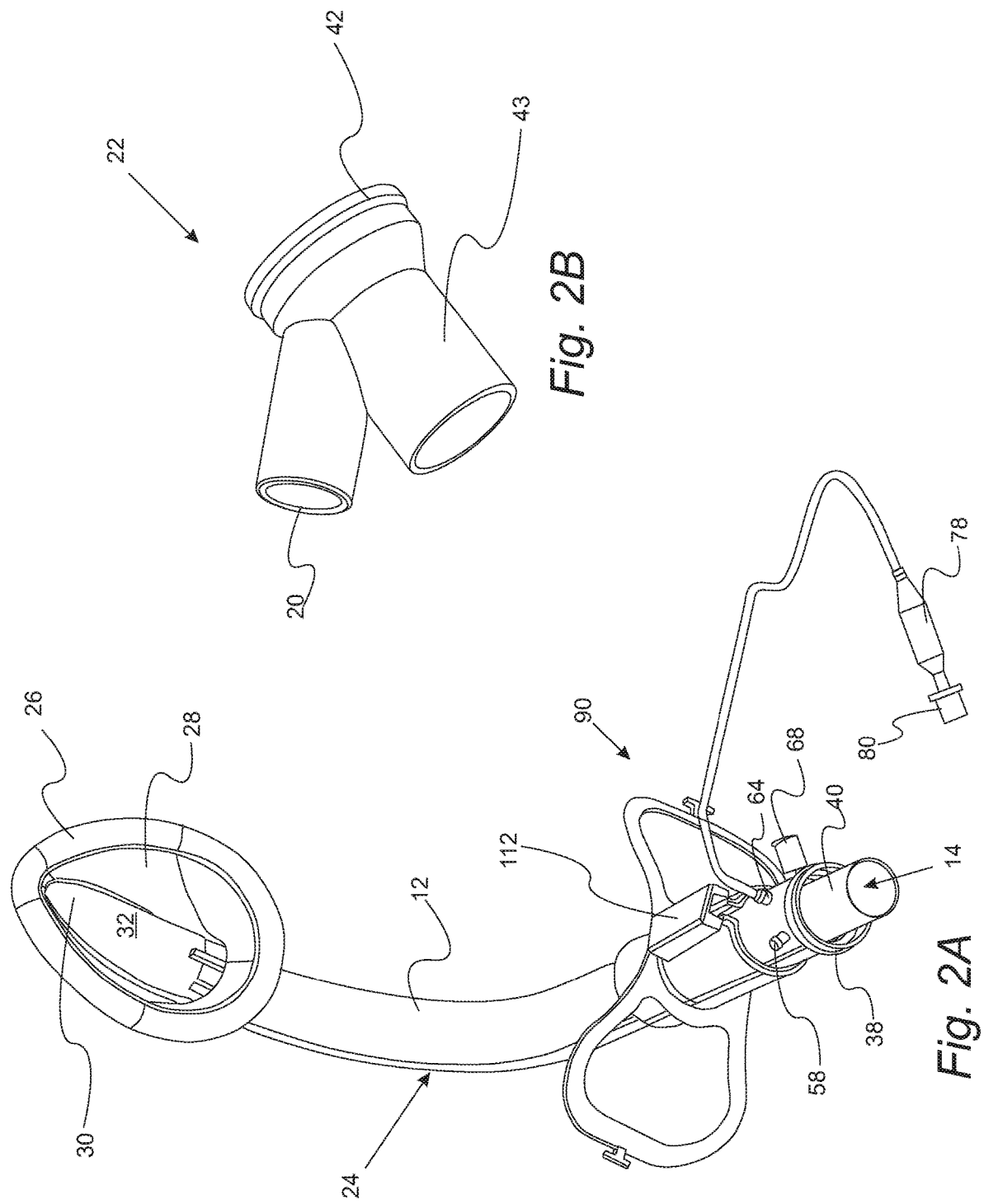
FIG. 2A is a perspective view of the courier airway device with the end component of the compound tubular structure removed.
FIG. 2B is a perspective view of the end component of the compound tubular structure.
Figure 3:
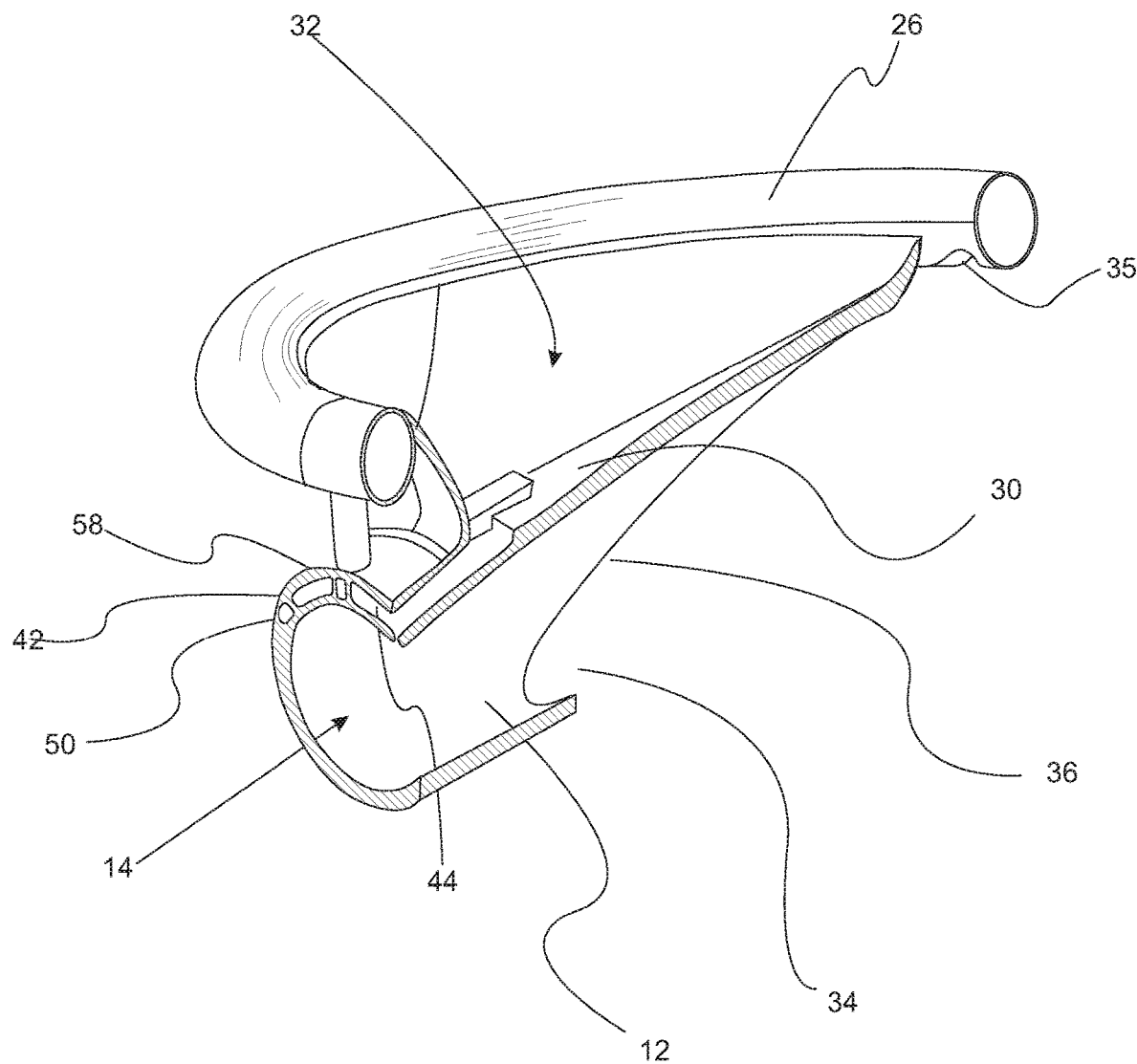
FIG. 3 is a cutaway perspective view of the courier airway device in the vicinity of the inflatable cuff.

Still referring to FIGS. 1, 2A, 2B, and 3, ventilation access port 20 can be a standardized male adaptor (e.g., a 15 mm adapter) for attachment to the standardized female attachment of an anesthetic circuit. Cuff 26 is attached to the distal central channel wherein the cuff 26 is an inflatable ring. In a refinement, cuff 26 is a tubular structure that defines a central cavity. Therefore, cuff 26 can be formed from a flexible material (e.g., plastics) so that when the cuff is deflated, the volume of the central cavity is smaller than when inflated. Examples of such flexible materials include, but are not limited to rubber-like elastic materials such as natural rubber, synthetic rubber, and elastomers. Synthetic rubber includes isoprene rubber, silicone rubber, urethane rubber, ethylene propylene rubber, and the like. Typically, the courier airway device 10 further includes peripheral wall 28 that attaches the tubular structure 12 to cuff 26. Peripheral wall 28 in combination with tube wall 30 and cuff 26 defines lumen 32 that provides a ventilating passage when cuff 26 is positioned about a patient's glottis. Central channel 14 has an outlet opening 34 from which a portion of the medical device emerges prior to reaching a distal portion of cuff. In another refinement central cannel 14 could be extended such that outlet opening 34 is at distal portion of cuff. Outlet opening 34 is physically separated from the lumen 32 by tube wall 30. In a refinement as depicted in FIG. 3, outlet opening 34 is an angular cutaway at end 36 of tubular structure 14. For example, tube wall 30 of tubular structure 12 can separate outlet opening 34 from lumen 32. In a refinement, cuff 26 includes a distal notch or series of notches 35 through which a portion of a medical device passes. Advantageously, the distal notch or series of notches reduced drag on the medical device as it passes.

Figure 4:
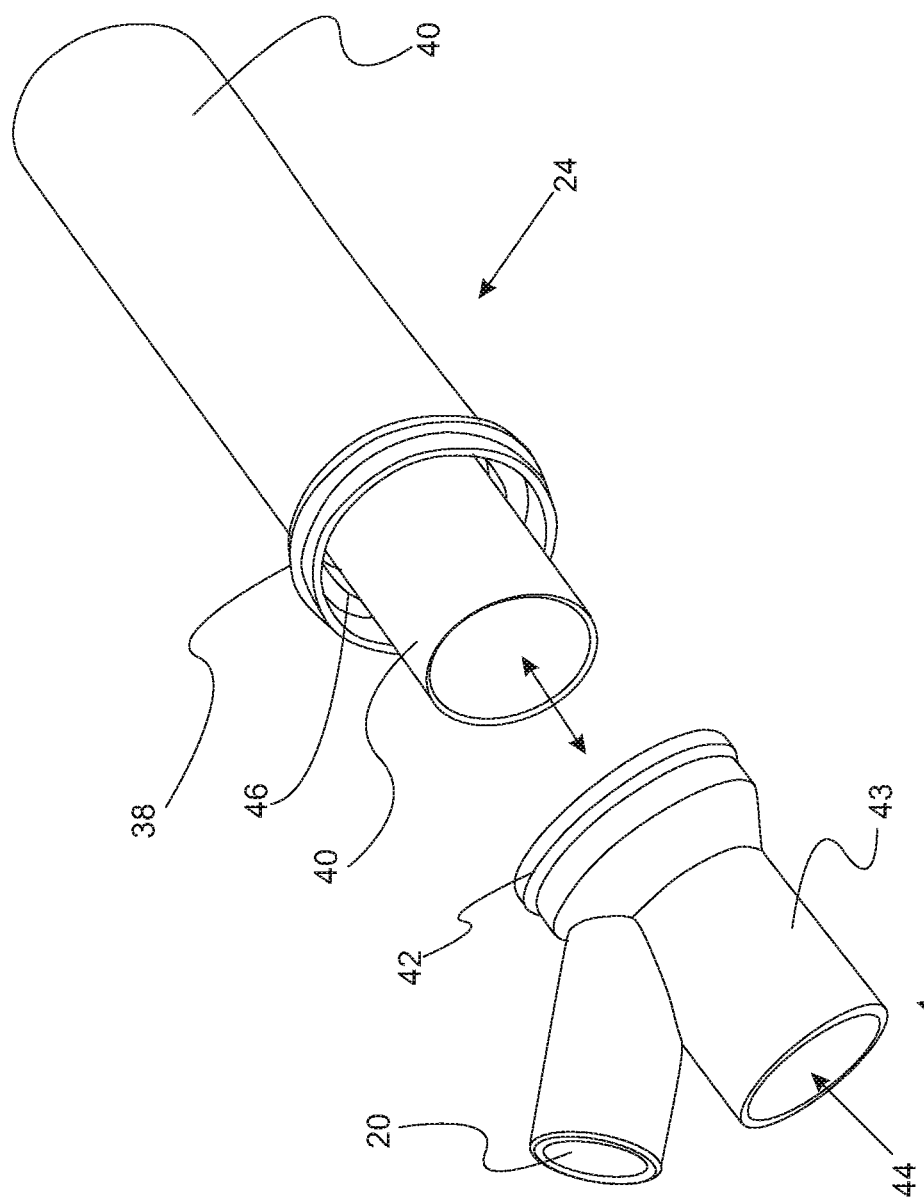
FIG. 4 is a perspective view showing the positioning of the tubular component in the end component to form the compound tubular structure.

FIG. 4 illustrates tubular component 24 attaching to end component 22. Tubular component 24 include flange 38 attached to tube section 40. End component 22 includes flange 42 attached to tube section 43 that mates to flange 38. Tube section 43 defined a central tube opening 44 (central channel 14 in FIG. 1). Tube end 46 of tube section 40 is positioned through central tube opening 44. However, after such placement a space 46 remains between flange 38 and tube end. This space is in communication with ventilation access port 20 and a series of channels defined by compound tubular structure 12 as set forth below.

Figure 5:
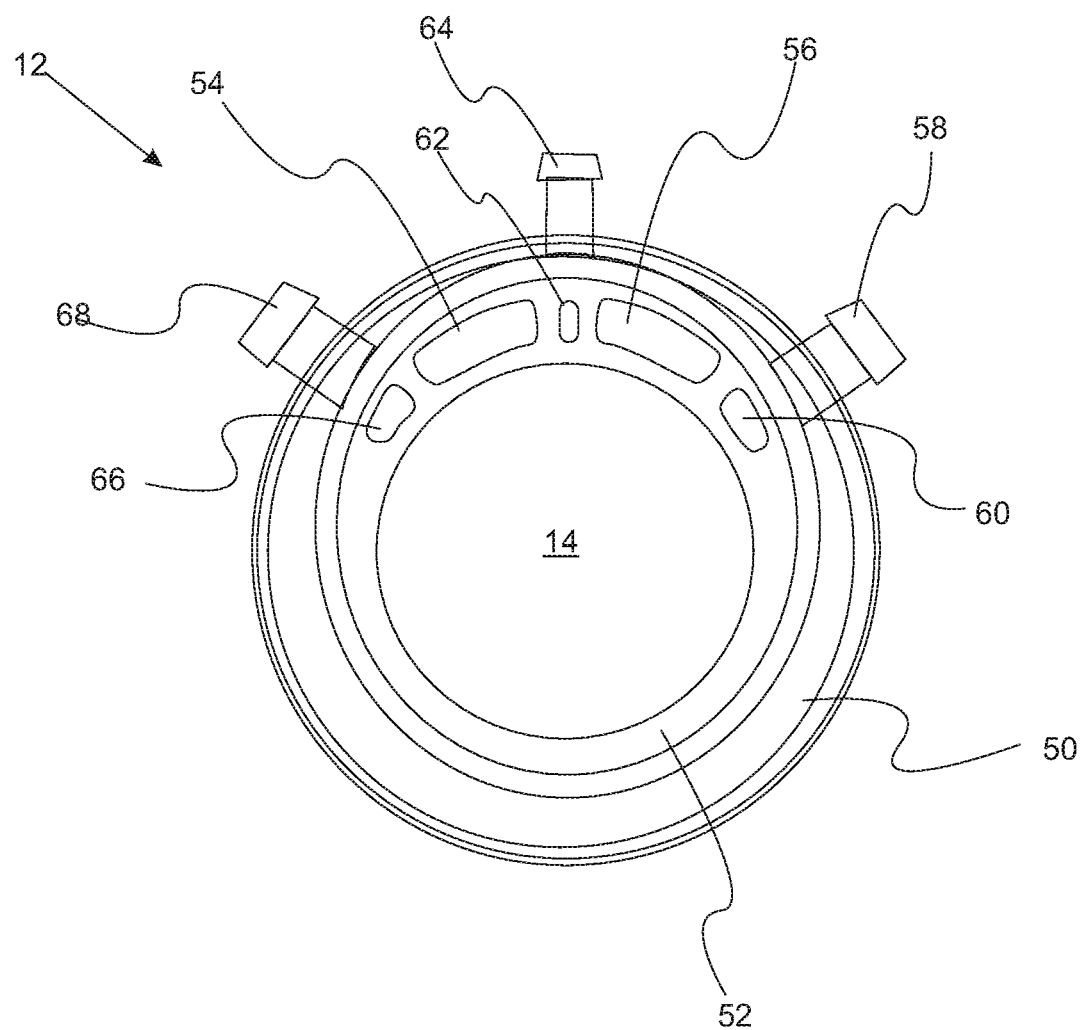
FIG. 5 is a cross section of a tubular structure which is part of the Courier airway device of FIG. 1.
Figure 6:
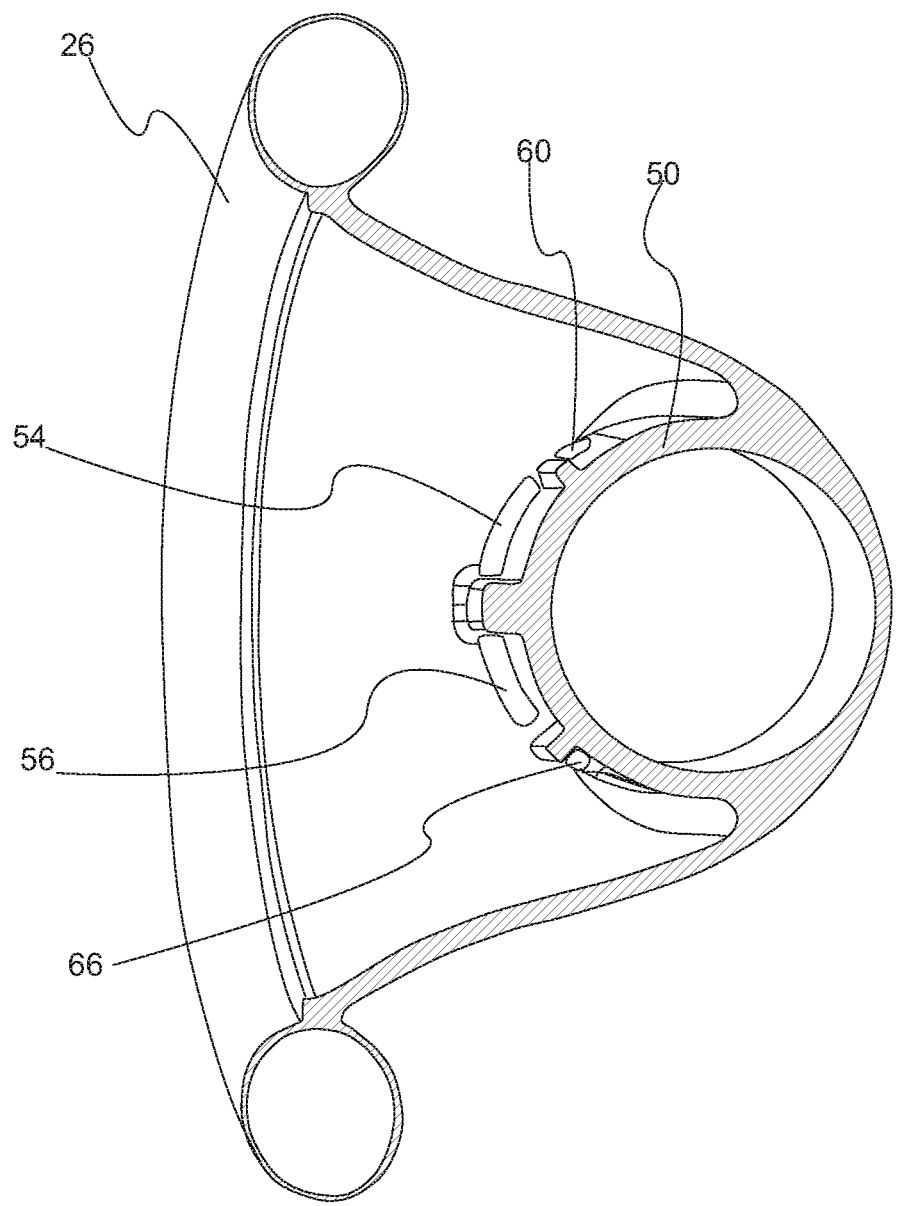
FIG. 6 is a perspective cross section showing the passages that open into the lumen of the cuff.
Figure 7:
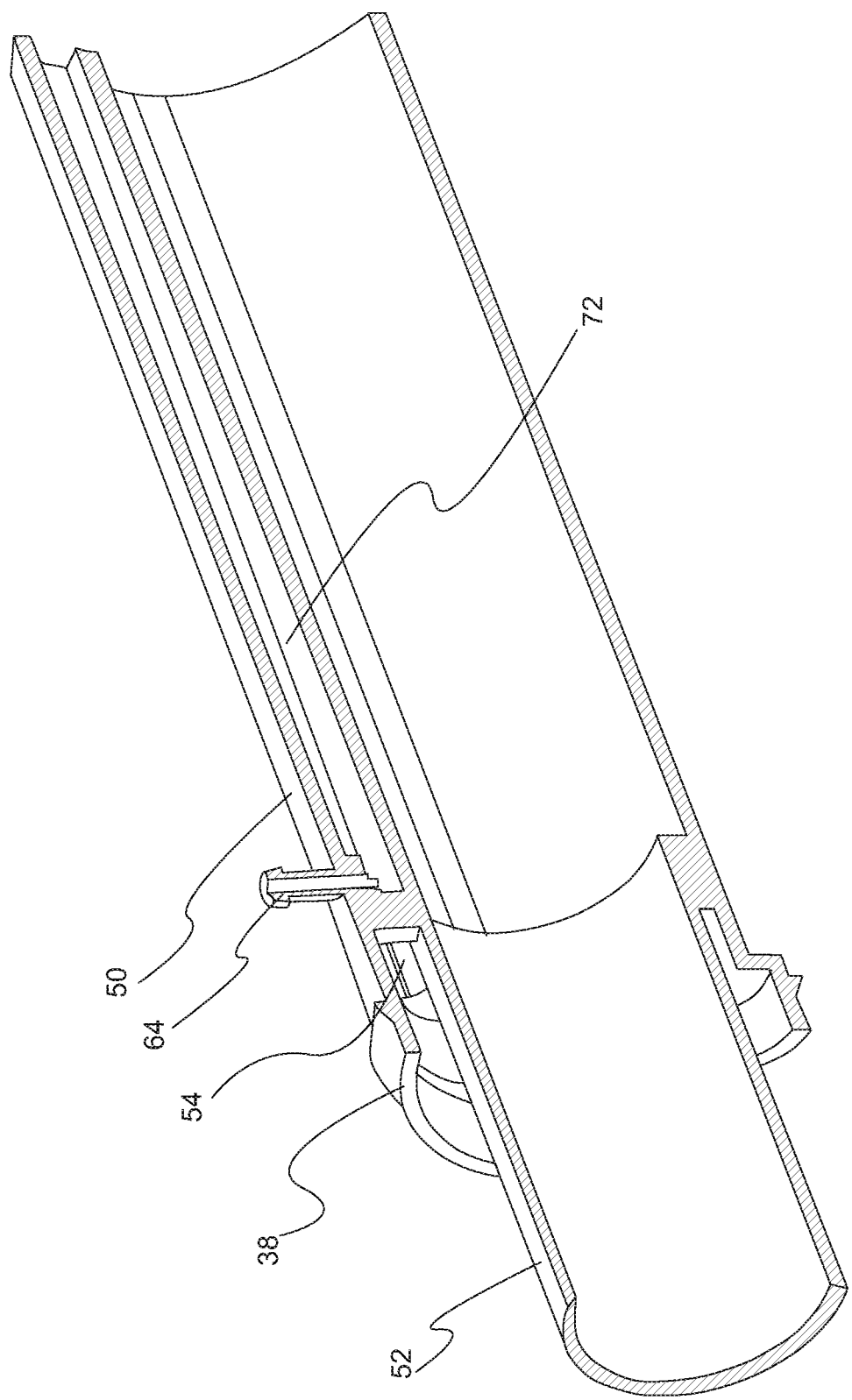
FIG. 7 is a perspective cross section of the tubular component.
Figure 8:
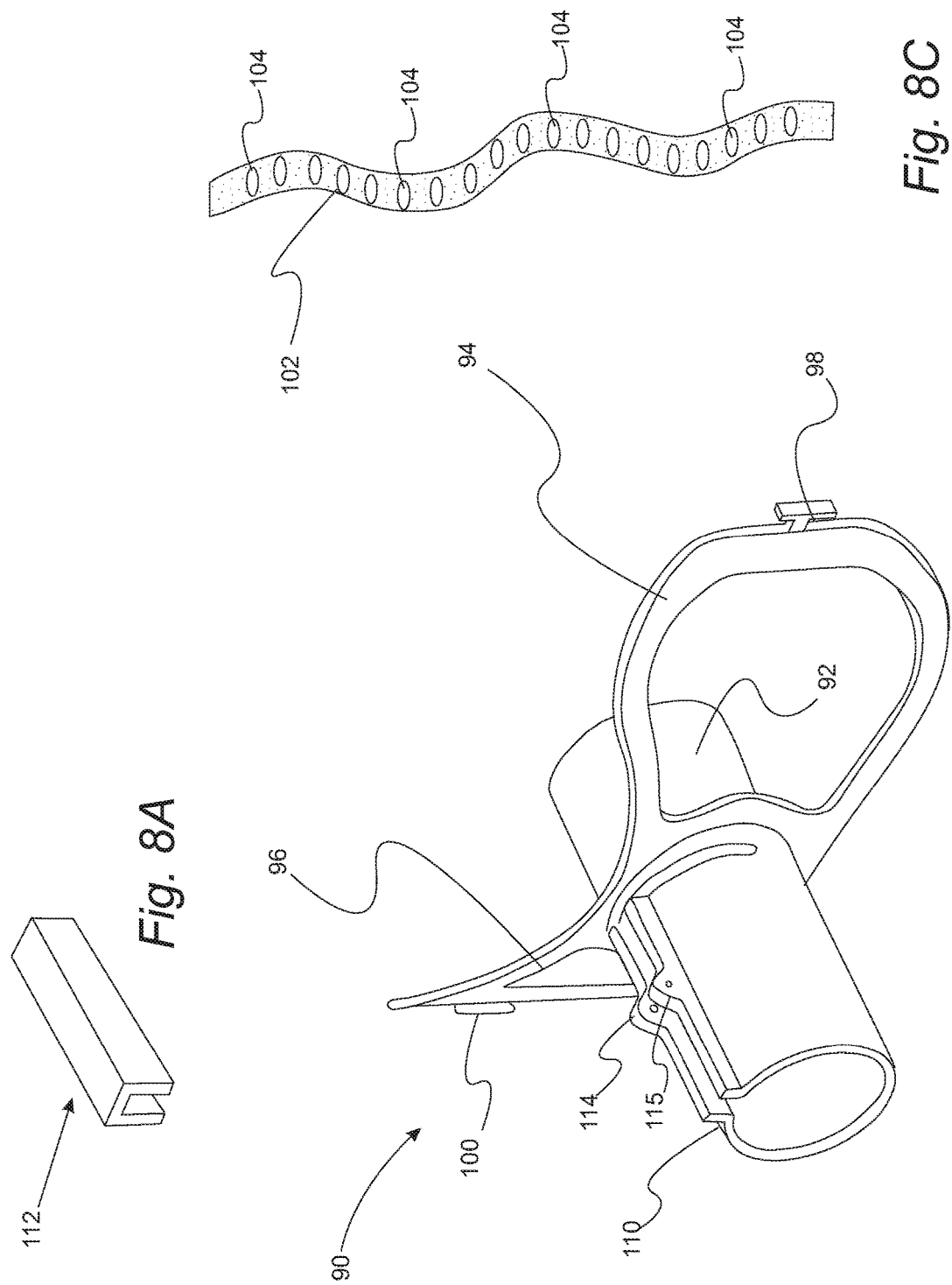
FIG. 8A is a perspective view of a locking cover to be attached to flanges on a bite block.
FIG. 8B is a perspective view of a bite block used to hold the courier airway device of FIG. 1 in place on a patient.
FIG. 8C is a top view of an adjustable strap to be attached to the bite block of FIG. 8B.

With reference to FIGS. 5, 6, and 7, illustrations of the channels defined by compound tubular structure 12 are provided. In a refinement, compound tubular structure 12 includes outer tube 50 and inner tube 52. In the vicinity of flange 38, outer tube 50 surrounds inner tube 52. Compound tubular structure 12 defines ventilation ducts 54, 56 which are in fluid communication with ventilation access port 20. Inner tube 52 also defines $CO_2$ sampling duct 66 allowing sampling of end tidal carbon dioxide ($ETCO_2$) at the level of a patient's glottis to monitor patient respirations. Compound tubular structure 12 includes a $CO_2$ access port 68 in communication with the $CO_2$ sampling duct 66 for obtaining an $ETCO_2$ sample from the patient. In a further refinement, compound tubular structure 12 further defines an auxiliary duct 60 for providing passive wall oxygen to the patient, the tubular structure including an oxygen inlet port 58 in communication with the auxiliary duct. In a refinement for the typical adult patient, the inner diameter of the inner tube 52 (i.e. central channel 14) can be from about 10 to 20 mm. In a further refinement, while the outer diameter of outer tube 50 can be from about 15 to 30 mm.

With reference to FIGS. 1, 2A, and 5, tubular structure 12 further defines a cuff inflation duct 62 for providing gas to the cuff 26 in order to inflate cuff 26. Tubular structure 12 also includes an inflation port/tube 64 in communication with the cuff inflation duct 62 for providing an inflation gas (e.g., air, nitrogen, etc.) thereto. Inflation port 64 in communication with integral one way check valve 78 which is also in fluid communication with adapter 80. In a refinement, a syringe is attached to check valve inflation adapter 80 and air is injected thereby inflating cuff 26. One way check valve 78 prevents deflation of cuff 26, for the duration of the case. For deflation, the syringe is attached to the inflation adapter 80 and the air may be aspirated at the end of the case allowing the courier airway device to be removed after deflation.

With reference to FIGS. 1, 8A, 8B, and 8C, the incorporation of a bite block 90 and locking mechanism 70 into the courier airway device is provided. Courier airway device 10 further includes an adjustable bite block 90 with associated locking mechanism 70 which minimizes movement of the courier airway device while the medical devise (e.g., an endoscope) is manipulated in and out of the upper gastrointestinal tract during a procedure. Locking mechanism 70 includes flanges 114, 115 of bite block 90 and locking cover 112. Bite block 90 includes bite tube 92 which is attached to pair of alae 94, 96 (i.e., wings) and bite tube extension 110. Bite block tube 92 surrounds tubular structure 12. Pair of alae 94, 96 includes attachment features 98, 100 (e.g., flanges) for attaching adjustable head strap 102 that holds courier airway device 10. Head strap 102 wraps around the patient's head and attaches to attachment features 98, 100 located on the lateral aspect of the alae via attachment holes 104. Head strap 102 secures courier airway device 10 to the patient's head. Head strap 102 is elastic and typically has a series of holes, every 1 to 2 cm to attach to flanges 98, 100 on alae 94, 96. Typically, alae 94, 96 are curved and conform to the patient's mouth and cheeks for comfort. In addition, alae 94, 96 are also sufficiently wide with an open structure to allow for visibility and suctioning of the patient's oral cavity as needed. Bite block tube 92 is lockable on tubular structure 12. In this regard, locking mechanism 70 is used to lock bite block tube extension 110 which uses locking cover 112 to decrease the diameter of bite tube extension 110 via flanges 114, 115 that can be forced together by locking cover 112. A unique attribute of locking mechanism 70 is that it has onehanded lock and release mechanism which enables quick and easy adjustment (advancement or retraction) of the tubular structure 12 so that cuff 26 remains seated properly over the glottis as needed.

Figure 9:
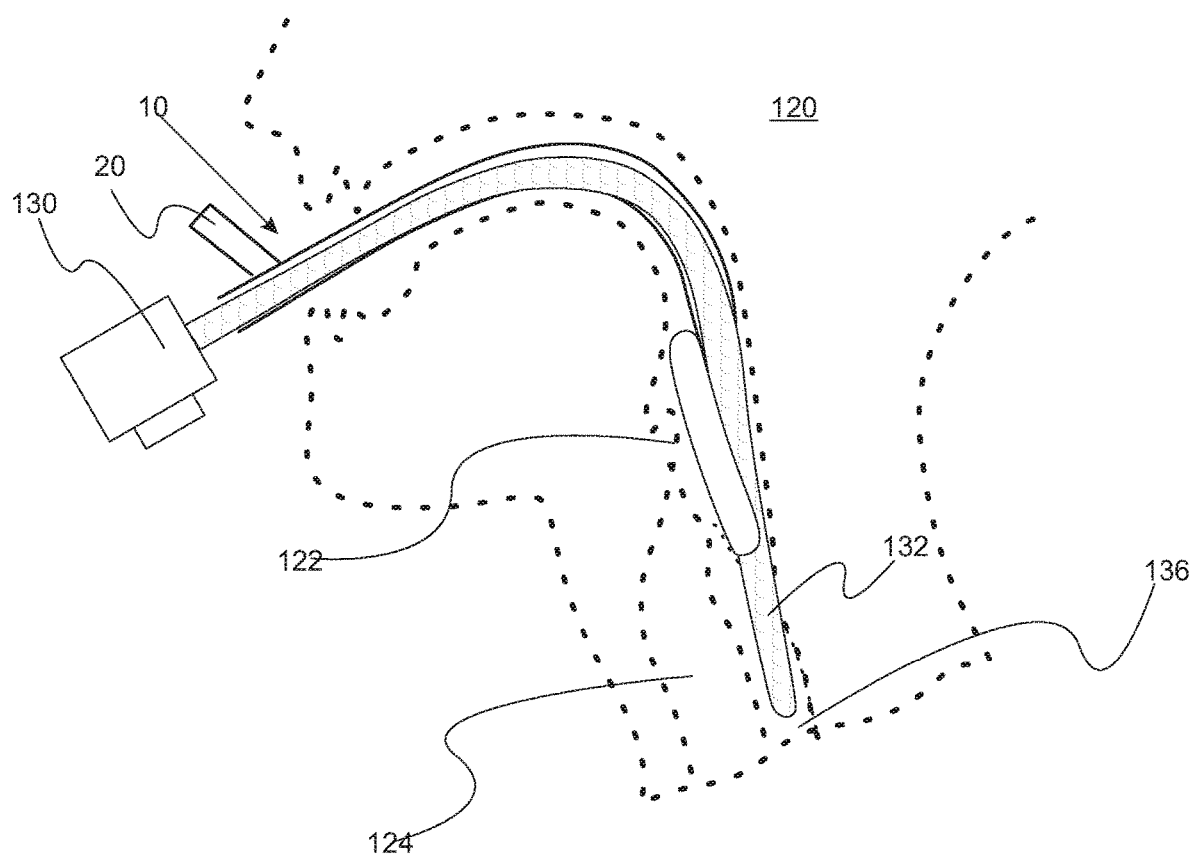
FIG. 9 is a schematic cross section of the courier airway device placed in a patient.

With reference to FIG. 9, a schematic cross section of the courier airway device placed in a patient is provided. Patient 120 has courier airway device 10 inserted into his airway with cuff 26 at the level of the patient's glottis 122 thereby allowing the controlled ventilation of trachea 124. Medical device 130 is inserted through the large central channel 14 with section 132 of the diagnostic device passing into the proximal region 136 of the esophagus. Of note, the angulated ventilation access port 20 is not in the central axis of the patient's oral cavity or the large central channel 14. This angulated ventilation access port 20 also swivels as indicated earlier and may be swiveled to the patients left, right or centrally for field avoidance of the anesthetic circuit, allowing better access for the proceduralist to the procedural field. This allows for "field avoidance" of the ventilator devices, and in one refinement allows the proceduralist to be less encumbered for access to his procedural field. In one refinement, the medical device 130 is a medical diagnostic device such as an endoscope. Therefore, a portion of the endoscope probe is moveably inserted into the central channel 14. In another refinement, the medical diagnostic device is a transesophageal echocardiogram. Therefore, a portion of transesophageal echocardiogram probe is moveably inserted into the central channel 14.

Figure 10:
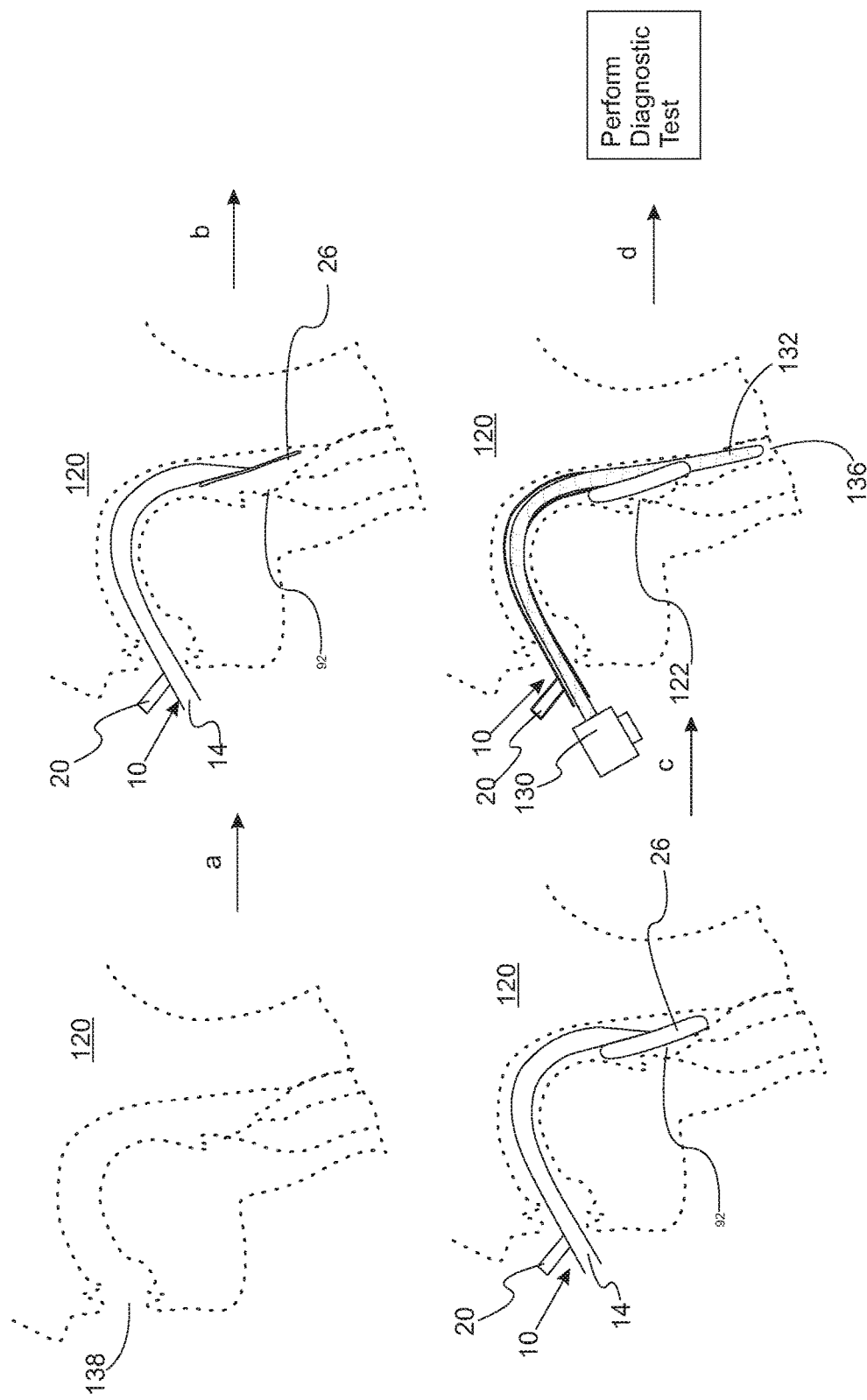
FIG. 10 is a schematic flowchart illustrating a diagnostic method using the medical diagnostic device.

With reference to FIG. 10, a schematic flowchart illustrating a method for performing a medical diagnostic test or a medical procedure on a subject using a courier airway device is provided. In step a), courier airway device 10 is positioned in the patient such that cuff 26 is at the level of a patient's glottis 122. Courier airway device 10 enters the patient 120 through the patient's oral cavity 138. At this stage, cuff 26 is typically deflated. In step b), cuff 26 is inflated after placement, bite block and alae are seated properly, head strap attached and locking mechanism secured. In step c), a portion of medical device 130 (e.g., endoscopic probe) is passed through the central channel 14 and into a position in a proximal region 136 of a patient's esophagus. In step d), the relevant medical diagnostic test or procedure can then be performed. In one refinement, the medical device 130 is an endoscope. In another refinement, the medical device 130 is a transesophageal echocardiogram device.

While exemplary embodiments are described above, it is not intended that these embodiments describe all possible forms of the invention. Rather, the words used in the specification are words of description rather than limitation, and it is understood that various changes may be made, without departing from the spirit and scope of the invention. Additionally, the features of various implementing embodiments may be combined to form further embodiments of the invention.

What is claimed is:

1. A courier airway device comprising:
   a tubular structure having a tube wall, the tubular structure defining a central channel having an outlet opening through which a medical device can be inserted into a proximal region of a patient's esophagus, the tubular structure also defining ventilation ducts positioned within the tube wall for providing gases from a controlled ventilation machine to a patient;
   a cuff attached to the central channel wherein the cuff is an inflatable ring; and
   a peripheral wall that attaches the tubular structure to the cuff, the peripheral wall in combination with the tube wall and cuff defining a lumen that provides a ventilating passage when cuff is positioned about a patient's glottis, wherein the outlet opening of the central channel is physically separated from the lumen by the tube wall.

2. The courier airway device of claim 1 wherein the tubular structure includes an end component rotatably attached to a tubular component, the tubular component having an access port attached thereto for providing gases from the controlled ventilation machine to a patient's trachea.

3. The courier airway device of claim 2 wherein the tubular component includes a first flange attached to a first tube section and the end component has a second flange attached to a second tube section, the second tube section defines a central opening through which the first tube section is positioned.

4. The courier airway device of claim 1 wherein the medical device emerges from the outlet opening prior to reaching a distal portion of the cuff and posterior to the cuff.

5. The courier airway device of claim 4 wherein the cuff includes a distal notch and/or series of notches through which a portion of the medical device passes, the distal notch and/or series of notches reducing drag on the medical device when passing through the tubular structure into the proximal region of the patient's esophagus.

6. The courier airway device of claim 5 wherein the tubular structure includes an angulated ventilation access port which swivels 360 degrees in communication with the ventilation ducts.

7. The courier airway device of claim 6 wherein the tubular structure further defines a $CO_2$ sampling duct allowing sampling of end tidal carbon dioxide at the level of the patient's glottis, the tubular structure including a $CO_2$ access port in communication with the $CO_2$ sampling duct for obtaining an end tidal carbon dioxide sample from the patient, the $CO_2$ sampling duct being positioned within the tube wall.

8. The courier airway device of claim 7 wherein the tubular structure further defines an auxiliary duct for providing wall oxygen to the patient at the level of the patient's glottis thereby substantially reducing dead space ventilation for the patient, the tubular structure including an oxygen inlet port in communication with the auxiliary duct.

9. The courier airway device of claim 8 wherein the tubular structure further defines a cuff inflation duct for providing gas to the cuff in order to inflate the cuff, the tubular structure including an inflation port in communication with the cuff inflation duct for providing an inflation gas to the cuff.

10. The courier airway device of claim 9 further comprising an integrated one way check valve in communication with the inflation port, the integrated one way check valve allowing for attachment of a syringe to inflate the cuff and further preventing deflation of the cuff.

11. The courier airway device of claim 10 further comprising a bite block attached to the tubular structure.

12. The courier airway device of claim 11 wherein the bite block includes a bite block tube that surrounds the tubular structure and a pair of alae attached to the bite block tube, the bite block tube being adjustable and lockable on the tubular structure.

13. The courier airway device of claim 12 wherein the pair of alae includes a feature for attaching an adjustable head strap to hold the bite block and therefore the courier airway device in place.

14. The courier airway device of claim 1 further comprising a portion of the medical device as an endoscope moveably inserted into and advanced through the central channel into the proximal region of the patient's esophagus.

15. The courier airway device of claim 1 further comprising a portion of transesophageal echocardiogram probe moveably inserted into and advanced through the central channel into the proximal region of the patient's esophagus.

16. The courier airway device of claim 1 wherein the ventilation ducts are separated from the central channel.

17. A method for performing a medical diagnostic test or a medical procedure on a subject using a courier airway device, the courier airway device comprising:
a tubular structure having a tube wall, the tubular structure defining a central channel having an outlet opening through which a medical device can be inserted into a proximal portion of a patient's esophagus, the tubular structure also defining ventilation ducts positioned within the tube wall for providing gases from a controlled ventilation machine to a patient;
a cuff attached to the central channel wherein the cuff is an inflatable ring; and
a peripheral wall that attaches the tubular structure to the cuff, the peripheral wall in combination with the tube wall and cuff defining a lumen that provides a ventilating passage when cuff is positioned about a patient's glottis, wherein the outlet opening is physically separated from the lumen by the tube wall, the method comprising:
positioning and securing the courier airway device in the patient such that the cuff is positioned and secured to remain at the level of the patient's glottis, the cuff entering the patient through a patient's oral cavity;
inflating the cuff;
inserting a portion of the medical device through the central channel and into position in a proximal region of the patient's esophagus; and
performing the medical diagnostic test or medical procedure.

18. The method of claim 17 wherein the medical device is an endoscope for viewing a patient's upper gastrointestinal tract.

19. The method of claim 17 wherein the medical device is a transesophageal echocardiogram device.

20. The method of claim 17 wherein the medical device emerges from the outlet opening prior to reaching a distal portion of the cuff and posterior to the cuff.

21. The method of claim 17 wherein the tubular structure includes an angulated ventilation access port which swivels and is in communication with the ventilation ducts.

22. The method of claim 21 wherein the tubular structure further defines a $CO_2$ sampling duct allowing sampling of end tidal carbon dioxide at the level of the patient's glottis, the tubular structure including a $CO_2$ access port in communication with the $CO_2$ sampling duct for obtaining an end tidal carbon dioxide sample from the patient, the $CO_2$ sampling duct being positioned within the tube wall.

23. The method claim 22 wherein the tubular structure further defines an auxiliary duct for providing wall oxygen to the patient at the level of the patient's glottis, the tubular structure including an oxygen inlet port in communication with the auxiliary duct.

24. The method of claim 23 wherein the tubular structure further defines a cuff inflation duct for providing gas to the cuff in order to inflate the cuff, the tubular structure including an inflation port in communication with the cuff inflation duct for providing an inflation gas through a one way check valve to the cuff.

25. A courier airway device comprising: a cuff that is an inflatable ring; a tubular structure having a tube wall, the tubular structure defining a central channel through which a medical device can be inserted into a proximal region of a patient's esophagus, the central channel having an outlet opening from which a portion of the medical device emerges prior to reaching a distal portion of the cuff, wherein the outlet opening is an angular cutaway at an end of the tubular structure, the tubular structure also defining ventilation ducts positioned within the tube wall for providing gases from a controlled ventilation machine to a patient, wherein the cuff is attached to the central channel; and a peripheral wall that attaches the tubular structure to the cuff, the peripheral wall in combination with the tube wall and cuff defining a lumen that provides a ventilating passage when cuff is positioned about a patient's glottis, wherein the outlet opening of the central channel is physically separated from the lumen by the tube wall.

* * * * *